(12) United States Patent
Chiriva-Internati (10) Patent No.: US 9,062,349 B2
(45) Date of Patent: Jun. 23, 2015

(54) COMPOSITION AND METHOD FOR DIAGNOSIS AND IMMUNOTHERAPY OF PROSTATE CANCER

(75) Inventor: Maurizio Chiriva-Internati, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 503 days.

(21) Appl. No.: 13/446,922

(22) Filed: Apr. 13, 2012

(65) Prior Publication Data

US 2012/0263757 A1    Oct. 18, 2012

Related U.S. Application Data

(60) Provisional application No. 61/475,395, filed on Apr. 14, 2011.

(51) Int. Cl.
| | | |
|---|---|---|
| C07K 16/00 | (2006.01) | |
| C12Q 1/68 | (2006.01) | |
| A61K 39/00 | (2006.01) | |
| G01N 33/574 | (2006.01) | |

(52) U.S. Cl.
CPC ........ *C12Q 1/6886* (2013.01); *C12Q 2600/158* (2013.01); *A61K 39/0011* (2013.01); *A61K 2039/5154* (2013.01); *G01N 33/57434* (2013.01); *G01N 33/57484* (2013.01)

(58) Field of Classification Search
None
See application file for complete search history.

(56) References Cited

U.S. PATENT DOCUMENTS

| 2010/0204055 A1 | 8/2010 | Bonner-Ferraby et al. |
| 2010/0260787 A1 | 10/2010 | Chiriva Internati et al. |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Ezzell (J. NIH Res. 1995 7:46).*
Spitler (Cancer Biotherapy, 1995, 10:1-3).*
Boon (Adv. Can. Res. 1992 58:177-210).*
(Haigh et al Oncology vol. 13 p. 1561 (1999).*
Allam, Mustapha, et al., "Enhancement of Th1 Type Cytokine Production and Primary T Cell Activation by PBI-1393," Clinical Immunology, (2007), 125:318-327.
Chiriva-Internati, M., et al., Successful Generation of Sperm Protein 17 (sp17)-Specific Cytotoxic T Lymphocytes from Normal Donors: Implication for Tumour-Specific Adoptive Immunotherapy Following Allogeneic Stem Cell Transplantation for Sp17-Positive Multiple Myeloma, Scan. J. Immunol. (2002), 56:429-433.
Chiriva-Internati, Maurizio, et al., "Sperm Protein 17 (Sp17) is a Suitable Target for Immunotherapy of Multiple Myeloma," Blood, Aug. 1, 2002, vol. 100, No. 3, pp. 961-965.
Chiriva-Internati, Maurizio, et al., "Tumor Vaccine for Ovarian Carcinoma Targeting Sperm Protein 17," Cancer, May 1, 2002, vol. 94, No. 9, pp. 2447-2453.
Chiriva-Internati, Maurizio, et al., "Identification of a Sperm Protein 17 CTL Epitope Restricted by HLA-A1," (2003), 107:863-865.
Chiriva-Internati, Maurizio, et al., Testing Recombinant Adeno-Associated Virus-Gene Loading of Dendritic Cells for Generating Potent Cytotoxic T Lymphocytes Against a Prototype Self-Antigen, Multiple Myeloma HM1.24, Blood, (2003), 102:3100-3107.
Chiriva-Internati, Maurizio, et al., "AKAP-4: a Novel Cancer Testis Antigen for Multiple Myeloma," British Journal of Haematology, (2007), 140:464-474.
Chiriva-Internati, Maurizio, et al., "The Pituitary Tumor Transforming Gene I (PTTG-1): An Immunological Target for Multuple Myeloma," Journal of Translational Medicine, (2008), 6:15, 9 pages.
Constantinou, J., et al., "PSA Testing: an Evolving Relationship with Prostate Cancer Screening," (2006), Prostate Cancer and Prostatic Diseases, 9:6-13.
Dannull, Jens, et al., "Prostate Stem Cell Antigen is a Promising Candidate for Immunotherapy of Advanced Prostate Cancer," Cancer Res., (2000), 60:5522-5528.
Drake, Charles G., "Prostate Cancer as a Model for Tumour Immunotherapy," Nat. Rev. Immunol., Aug. 2010, 10(8):580-593.
Dranoff, Glenn, "Targets of Protective Tumor Immunity," Cancer Vaccines, (2009), 1174:74-80.
Ebelt, Kathleen, et al., "Dominance of CD4+ Lymphocytic Infiltrates with Disturbed Effector Cell Characteristics in the Tumor Microenvironment of Prostate Carcinoma," The Prostate, (2008), 68:1-10.
Ferlay, J., et al., "Estimates of the Cancer Incidence and Mortality in Europe in 2006," Anals of Oncology, (2007), 18 (3):581-592.
Garcia-Hernandez, Maria de la Luz, et al., "Prostate Stem Cell Antigen Vaccination Induces a Long-Term Protective Immune Response against Prostate Cancer in the Absence of Autoimmunity," Cancer Research, Feb. 1, 2008, 68(3):861-869.
Grizzi, Fabio, et al., "Sperm Protein 17 is Expressed in Human Nervous System Tumours," BMC Cancer, (2006), 6:23, 7 pages.
Hildner, Kai, et al., "Batf3 Deficiency Reveals a Critical Role for CD8a+ Dendritic Cells in Cytotoxic T Cell Immunity," Science, Nov. 14, 2008, 322(5904):1097-1100.
Jager, D., et al., "Immune Responses to Tumour Antigens: Implications for Antigen Specific Immunotherapy of Cancer," (2001), J. Clin. Pathol., 54:669-674.
Jin, Jing, et al., "Proteomic, Functional, and Domain-Based Analysis of in Vivo 14-3-3 Binding Proteins Involved in Cytoskeletal Regulation and cellular Organization," Current Biology, Aug. 24, 2004, vol. 14, pp. 1436-1450.
Korangy, Firouzeh, et al., "Spontaneous Tumor-Specific Humoral and Cellular Immune Responses to NY-ESO-1 in Hepatocellular Carcinoma," Clin. Cancer Res., (2004), 10:4332-4341.
Lee, Soo Ok, et al., "Interleukin-4 Stimulates Androgen-Independent Growth in LNCaP Human Prostate Cancer Cells," (2008), The Prostate, 68:85-91.
Lefievre, Linda, et al., "Counting Sperm Does Not Add Up Any More: Time for a New Equation?" Reproduction, (2007), 133:675-684.
Lim, Seah H., et al., Sperm Protein 17 is a Novel-Testis Antigen in Multiple Myeloma, (2001), 97:1508-1510.
Liu, WM, et al., "Pre-Treatment with Chemotherapy can Enhance the Antigenicity and Immunogenicity of Tumours by Promoting Adaptive Immune Responses," British Journal of Cancer, (2010), 102:115-123.

(Continued)

*Primary Examiner* — Sheela J Huff
(74) *Attorney, Agent, or Firm* — Chainey P. Singleton; Edwin S. Flores; Chalker Flores, LLP (57) ABSTRACT

A method and composition for the diagnosis of and treatment of prostate cancer including a recombinant AKAP-4 tumor-associated antigen loaded antigen presenting cell that generates an AKAP-4 specific cytotoxic T lymphocyte specific for one or more prostate cancer cells.

8 Claims, 7 Drawing Sheets

(56) References Cited

OTHER PUBLICATIONS

Lu, Jun, et al., "Recognition of Prostate Tumor Cells by Cytotoxic T Lymphocytes Specific for Prostate-Specific Membrane Antigen," (2002), Cancer Res., 62:5807-5812.

McNeel, Douglas G., et al., "Antibody Immunity to Prostate Cancer Associated Antigens can be Detected in the Serum of Patients with Prostate Cancer," The Journal of Urology, Nov. 2000, vol. 164, pp. 1825-1829.

Miller, Ashley M., et al., CD4+CD25high T Cells are Enriched in the Tumor and Peripheral Blood of Prostate Cancer Patients, (2006). J. Immunol. 177:7398-7405.

Parmigiani, Raphael B., et al., "Characterization of a Cancer/Testis (CT) Antigen Gene Family Capable of Eliciting Humoral Response in Cancer Patients," Nov. 28, 2006, PNAS, vol. 103, No. 48, pp. 18066-18071.

Sabbisetti, Venkata S., et al., "Calcitonin Increases Invasiveness of Prostate Cancer Cells: Role for Cyclic AMP-Dependent Protein Kinase A in Calcitonin Action," (2005), Int. J. Cancer, 117:551-560.

Santin, Alessandro D., et al., Induction of Human Papillomavirus-Specific CD4 + and CD8+ Lymphocytes by E7-Pulsed Autologous Dendritic Cells in Patients with Human Papillomavirus Type 16- and 18-Positive Cervical Cancer, J. Virol., Jul. 1999, vol. 73, No. 7, pp. 5402-5410.

Scanlan, Matthew J., et al., "The Cancer/Testis Genes: Review, Standardization and Commentary," Cancer Immunity, Jan. 23, 2004, vol. 5, 15 pages.

Straughn, Jr., J. Michael, et al., "Expression of Sperm Protein 17 (Sp17) in Ovarian Cancer," Int. J. Cancer, (2004), 108:805-811.

Thompson, Ian M., et al., "Prevalence of Prostate Cancer Among Men with a Prostate-Specific Antigen Level $\leq$ 4.0 ng per Milliliter," The New England Journal of Medicine, May 27, 2004, vol. 350, No. 22, 8 pp. 2239-2246.

Turner, Regina M., et al., "Molecular Genetic Analysis of Two Human Sperm Fibrous Sheath Proteins, AKAP4 and AKAP3, in Men with Dysplasia of the Fibrous Sheath," Journal of Andrology, Mar./Apr. 2001, vol. 22, No. 2, pp. 302-315.

Yang, Jae Seung, et al., "Endotoxin Contamination in Commercially Available Pokeweed Mitogen Contriburtes to the Activation of Murine Macrophages and Human Dendritic Cell Maturation," Clinical and Vaccine Immunology, Mar. 2006, vol. 13, No. 3, pp. 309-313.

Zhou, He, et al., "T Cell-Mediated Suppression of Angiogenesis Results in Tumor Protective Immunity," Blood, (2005), 106:2026-2032.

Zhu, Jinfang, et al., "Heterogeneity and Plasticity of T Helper Cells," Cell Research (2010), 20:4-12.

\* cited by examiner

FIG. 3A
TESTIS (+ ctrl)

FIG. 3B
NORMAL PROSTATE

SEQUENCE LISTING

<160> NUMBER OF SEQ ID NOS: 4

<210> SEQ ID NO 1
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 1
gcgtactctg atactacaat gatg        24

<210> SEQ ID NO 2
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 2
ggggtttggg gtaaagtca        19

<210> SEQ ID NO 3
<211> LENGTH: 27
<212> TYPE: DNA
<213> ORGANISM: artificial sequence
<220> FEATURE:
<223> OTHER INFORMATION: synthetic oligonucleotide

<400> SEQUENCE: 3
ggatccagaa aacatcattc cagggtc        27

<210> SEQ ID NO 4
<211> LENGTH: 29
<212> TYPE: DNA
<213> ORGANISM: artificial sequence
<220> FEATURE:
<223> OTHER INFORMATION: synthetic oligonucleotide

<400> SEQUENCE: 4
ggtaccaggg gggtaagatg aagaggagt        29

COMPOSITION AND METHOD FOR DIAGNOSIS AND IMMUNOTHERAPY OF PROSTATE CANCER

CROSS-REFERENCE TO RELATED APPLICATIONS

This application claims priority based on U.S. Provisional Application No. 61/475,395, filed Apr. 14, 2011. The contents of which is incorporated by reference in its entirety.

TECHNICAL FIELD OF THE INVENTION

One embodiment of the present invention relates in general to the field of detection of prostate cancer and immunotherapy thereof, specifically to methods and compositions for diagnosis and treatment of prostate cancer using cancer/testis antigen, AKAP-4 compositions.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with methods and compositions for diagnosis and treatment of prostate cancer.

Prostate cancer is the second most common cancer in older men, after skin cancer. Despite major efforts in the last 20 years to improve detection and therapies, prostate cancer is still a leading cause of morbidity and death in men throughout the world, e.g., 192,280 new prostate cancer diagnoses with 27,360 related deaths are estimated in the United States and even higher in the European Union with 301,500 new cases and 67,800 deaths expected every year (1). Unlike 20 years ago when more than 50% of men newly diagnosed with prostate cancer displayed metastases, today the majority are confined to the prostate gland (2). Such diagnostic improvement was due to the development of new screening techniques for earlier prostate cancer detection based on tumor biomarkers.

Prostate specific antigen (PSA) is the best known prostate cancer biomarker, introduced in 1986 (3) and FDA-approved in 1994 (4). However, growing evidence indicates that PSA testing is less than ideal as a screening technique for prostate cancer detection, since it suffers from high false positive and false negative rates, causing healthy men to undergo unnecessary prostate biopsies in 75% of cases (5), and about 27% of cancer-bearing men to be misdiagnosed (6).

Prostate cancer is difficult to diagnose because the prostate specific antigen screening method is associated with many false positives. In addition there is a need to develop new and more effective treatments. Among presently available new treatments, immunotherapy is a promising approach. The expression of the cancer/testis antigen, AKAP-4, was tested in prostate cancer patients to evaluate the possibility of exploiting AKAP-4 as a target for immunotherapy.

SUMMARY OF THE INVENTION

One embodiment of the present invention provides treatments, immunotherapies, diagnostics and compositions for the treatment of Prostate cancer including the cancer/testis antigen, AKAP-4.

The present invention provides a composition for the treatment of prostate cancer including a recombinant AKAP-4 tumor-associated antigen loaded antigen presenting cell that generates an AKAP-4 specific cytotoxic T lymphocyte specific for one or more prostate cancer cells. The antigen presenting cell may be a dendritic cell and more specifically an autologous dendritic cell. The recombinant AKAP-4 tumor-associated antigen may be in the form of a vaccine composition and the vaccine composition may be a nucleotide sequence that codes for the recombinant AKAP-4 tumor-associated antigen.

The present invention also includes a method for identifying a human subject suspected of having subject or at least at risk of developing prostate cancer by obtaining a sample from the subject; and determining the presence or absence of a specific anti-AKAP-4 immunoglobulins in the sample, wherein the presence of the specific anti-AKAP-4 immunoglobulins in the sample indicating the subject is afflicted with or at least at risk of developing prostate cancer.

The present invention also includes a method for the determination of the tumor marker profile of an individual suffering from cancer by contacting a sample of bodily fluids from the individual with a AKAP-4 tumor-associated antigen; determining the presence or absence of a complex of the AKAP-4 tumor-associated antigen bound to one or more autoantibodies present in the sample of bodily fluids, wherein the one or more autoantibodies being immunologically specific to the AKAP-4 tumor-associated antigen; wherein the presence of the complex provides the tumor marker profile of the individual, and wherein the tumor marker profile is determined as an indication of the course of disease. The presence of the complex indicates the detection of cancer. The cancer is prostate cancer.

The present invention also includes an immunotherapy composition for the treatment of cancer comprising an AKAP-4 tumor-associated antigen capable of generating an AKAP-4 specific cytotoxic T lymphocyte specific for one or more prostate cancer cell. The immunotherapy composition may further include at least one antigen presenting cell and more specifically the antigen presenting cell is a dendritic cell. The antigen presenting cell is a pulsed or loaded with the peptide or an expression construct encoding the AKAP-4 tumor-associated antigen.

The present invention also includes a method for detecting prostate cancer in a subject by obtaining a sample from the subject; and determining the presence or absence of AKAP-4 in the sample, wherein the presence of AKAP-4 in the sample indicating the subject is afflicted with or at least at risk of developing prostate cancer.

The present invention includes a composition including an immunostimulatory nucleic acid vector comprising the nucleotide sequence coding for an AKAP-4 tumor-associated antigen and the nucleic acid vector is separate from the immunostimulatory nucleic acid or the antigen is a peptide antigen.

The present invention also includes a method for the treatment of cancer by administration to a mammal in need thereof a synergistic, therapeutically effective amount of a cancer/testis antigen, in addition to one or more diluents, vehicles, excipients, and/or inactive ingredients; generating a specific cytotoxic T lymphocytes (CTL) from the cancer/testis antigen; and targeting one or more tumor cells with the specific cytotoxic T lymphocytes and the the cancer/testis antigen may be AKAP-4.

One embodiment of the present invention is directed to the expression of the cancer/testis antigen, AKAP-4, in prostate cancer patients to evaluate the possibility of exploiting AKAP-4 as a target for adoptive immunotherapy or antitumor vaccine. The aberrant expression of AKAP-4 in prostate cancer could potentially be developed as a biomarker in prostate cancer.

BRIEF DESCRIPTION OF THE DRAWINGS

For a more complete understanding of the features and advantages of one embodiment of the present invention, reference is now made to the detailed description of the invention along with the accompanying figures and in which.

DETAILED DESCRIPTION OF THE INVENTION

While the making and using of various embodiments of one embodiment of the present invention are discussed in detail below, it should be appreciated that one embodiment of the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to one embodiment of the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Prostate cancer remains the second most common cancer after skin cancer in men worldwide and is characterized by a high mortality rate, despite ongoing advances in diagnostic and therapeutic techniques. One embodiment of the present invention provides alternative approaches of prostate cancer treatment using the cancer/testis antigen AKAP-4 for immunotherapy or tumor vaccination in the management of prostate cancer.

One embodiment of the present invention provides diagnostic compositions, immunotherapy compositions, antitumor compositions, and diagnostics for prostate cancer using an AKAP-4 biomarker in prostate cancer. For example, one embodiment of the present invention provides an AKAP-4 immunotherapy composition for prostate cancer in the form of an adoptive vaccination.

AKAP-4 was shown both at the cytoplasmic and surface levels of the LnCAP prostate cancer cell line. AKAP-4 was also highly expressed in prostate cancer cells from patients. Specific anti-AKAP-4 circulating immunoglobulins were detected in AKAP-4 positive subjects. By using recombinant AKAP-4 loaded autologous dendritic cells, we generated AKAP-4 specific and HLA-1 restricted cytotoxic T lymphocytes able to kill prostate cancer cells in vitro. Further characterization indicated a Th-1 skewing in the cytokine secretion profile of these cells.

One embodiment of the present invention demonstrates the aberrant expression of AKAP-4 in prostate cancer, which will potentially be developed as a biomarker in prostate cancer and AKAP-4 is a potential target for prostate cancer adoptive immunotherapy or antitumor vaccination.

The present inventors recognized the ability of one embodiment of the present invention to exploit tumor associated antigens not only for screening purposes but also as targets for tumor immunotherapy underlines their relevance in oncology and is due to features frequently shared by molecular biomarkers and tumor antigens: unique or highly tumor cell restricted expression and ability to elicit immune responses in tumor-bearing individuals.

To date, only a small panel of immunogenic prostate cancer-associated antigens has been identified, including Prostate Stem Cell Antigen (PSCA), Prostate Specific Membrane Antigen (PSMA), Prostatic Acid Phosphatase (PAP), and Prostrate Specific Antigen (PSA) itself (12-15). Several studies indicate that cancer/testis antigens (CTA) represent the most attractive tumor associated-antigen class for immunotherapy approaches because of their potent immunogenicity and tumor-restricted expression (16-19). In addition, CTA can be successfully used to generate specific cytotoxic T lymphocytes (CTL) targeting tumor cells in vitro and in vivo (17, 20-23). However, the panel of currently known CTA in prostate cancer is limited (24-28).

The CTA A-kinase anchor proteins (AKAPs) are a growing family of scaffolding proteins able to control intracellular signals by affecting cyclic AMP-dependent protein kinase-A (PKA) (29, 30). AKAP 4 has been identified as an immunogenic CTA in 42% of multiple myeloma patients (31), and is known to play a critical role in prostate cancer cell invasiveness (32). Here we show for the first time aberrant expression of AKAP-4 in LnCAP prostate cancer cells and in prostate cancer biopsies. Further, we demonstrate AKAP-4 immunogenicity in patients and the successful generation of AKAP-4-specific Cytotoxic T-lymphocyte (CTL) responses are able to selectively kill prostate cancer cells.

The present inventors analyzed normal prostate tissues, 15 patients with prostate cancer and the LnCAP prostate cancer cell line by immunohistochemistry and tested AKAP-4 immunogenicity through indirect Enzyme-Linked Immunosorbent Assay (ELISA) on sera from patients and healthy subjects, and generated in vitro AKAP-4-specific cytotoxic lymphocytes from peripheral blood mononuclear cells.

AKAP-4 was shown both at the cytoplasmic and surface levels of the LnCAP prostate cancer cell line. AKAP-4 was also highly expressed in prostate cancer cells from patients. Specific anti-AKAP-4 circulating immunoglobulins were detected in AKAP-4 positive subjects. By using recombinant AKAP-4 loaded autologous dendritic cells, we generated AKAP-4 specific and HLA-I restricted cytotoxic T lymphocytes able to kill prostate cancer cells in vitro. Further characterization indicated a Th-1 skewing in the cytokine secretion profile of these cells.

The human prostate carcinoma cell line LnCAP was purchased from the American Type Culture Collection (ATCC) (Manassas, Va., USA), maintained at 37 OC and 5% $CO_2$ in ATCC-formulated RPMI-1640 Medium (Catalog No. 30-2001) supplemented with 10% fetal bovine serum (FBS) (Invitrogen Corp, Carlsbad, Calif., USA). Cells were subcultured at a 1:3 ratio twice a week and used within 2 passages after thawing for described analyses.

AKAP-4 protein expression in 15 prostate cancer biopsy samples and in normal prostate and testis tissues (Pantomics, San Francisco, Calif., USA) were evaluated. Clinical materials were obtained with approval from the local ethics committee and the patients' informed consent prostate cancer cells were isolated from biopsies as described elsewhere (33, 34). Briefly, punch biopsies were minced and tissue fragments were plated in epithelial cell selective medium (RPMI 1640 medium supplemented with 2.5% charcoal-stripped, heat-inactivated FBS, 20 mM HE PES buffer, 100 units/mL penicillin, 100 mg/ml streptomycin, 0.25 mg/ml amphotericin B, 50 mg/ml gentamycin, 56 mg/ml bovine pituitary extract, 1× insulin-transferrin-selenium, 10 ng/mL epidermal growth factor, and 50 ng/mL cholera toxin). Cells were maintained in 5% $CO_2$ and 37° C. for 24 hours prior to analysis.

Reverse transcriptase polymerase chain reaction (RT-PCR) for AKAP-4 mRNA expression. PCR analysis was performed as previously described (23, 31). Briefly, 1 μg of total RNA extracted from cells by Tri-reagent (Sigma, St Louis, Mo., USA) was DNAse I digested (Ambion, Austin, Tex., USA) and reverse-transcribed by random hexamers. The primer sequences were as follows: 5'-GCG TAC TCT GAT ACT ACA ATG ATG-3' (SEQ ID NO: 1) and 5'-GGG GTT TTG GGT AAA GTC A-3' (SEQ ID NO: 2) (35 cycles, 55° C. annealing temperature). PCR products were visualized on an ethidium bromide agarose gel for a DNA band of the expected size. All results were confirmed in 3 independent RT-PCRs.

Generation of recombinant AKAP-4 protein. Total RNA from the LnCAP cell line was used to obtain AKAP-4 cDNA by RT-PCR. RNA was isolated by TRizol (Gibco BRL Life Sciences Technologies, Rockville, Md.) and treated with 10 U/μg RNAse-free DNase I (Promega, Madison, Wis.) for 1 hour at 37° C. mRNA was then isolated through Oligotex mRNA kit (Qiagen, Valencia, Calif.). First-strand cDNA synthesis was performed at 37° C. for 1 hour in a final reaction volume of 25 μL (0.5 μg mRNA; 50 mM Tris-HCl, pH 8.3; 75 mM KCl; 3 mM MgCl2; 10 mM DTT; 0.5 μM oligo-dT; 0.5 mM each of the four dNTPs; 30 U RNasin ribonuclease inhibitor; 200 U M-MLV reverse transcriptase). PCR amplification of the cDNA was performed in a 100 μL reaction volume containing 2.5 U Takara Z-Taq polymerase, according to the manufacturer's protocol (Takara Shuzo, Otzu, Japan). The AKAP-4 primer sets were upstream 5'-GGATCCAGAAAACATCATTCCAGGGTC-3', (SEQ ID NO: 3) downstream 5'-GGTACCAGGGGGGTAAGATGAAGAGGAGT-3' (SEQ ID NO: 4) and targeted the complete human AKAP-4 coding sequence. Using Bam H-I and Kpn-I restriction sites, AKAP-4 cDNA was then cloned into the PQE30 plasmid vector for 6-His-tagged recombinant AKAP-4 protein expression in M15 E. coli cells. 6-His-tagged recombinant AKAP-4 was isolated through the Ni-NTA Spin Columns (Qiagen, CA, USA) according to the manufacturer's directions. AKAP-4 protein was endotoxin-free, as confirmed by endotoxin detection assay performed through TOXIN-SENSOR™ Chromogenic LAL Endotoxin Assay Kit (GenScript USA Inc., 08854, NJ, USA) (35).

Immunohistochemistry. Two μm thick paraffined sections were cut from the biopsy samples and processed as previously described (36). After deparaffining and rehydrating, the sections underwent antigen retrieval for 45 min at 98° C. in EDTA 1 mM, incubated with 3% $H_2O_2$ for 15 minutes, and then treated with mouse anti-human AKAP-4 primary antibody (Santa Cruz Biotechnology, 1:100 dilution) at room temperature for two hours, or with 1 mg/mL mouse lgG2a (Dako, USA) as a negative control. This was followed by 30 minutes incubation with the DAKO Envision system (DAKO, Glostrup, Denmark). 3,3'-diaminobenzidine tetrahydrochloride (Sigma Ltd, Missouri, USA) was used as a chromogen to yield brown reaction products. The nuclei were counterstained with hematoxylin solution (DAKO).

Immunocytochemistry and immunofluorescence. 5×104 to 105 prostate cancer cells were spun in a cytospin column. After SlideRite (Fisher, USA) fixing and overnight air drying, each sample was permeabilized in a 0.1% Triton X-100 sodium citrate buffer for 15 minutes at 4° C., or left nonpermeabilized. For immunocytochemistry, cells were exposed to the anti-AKAP-4 primary antibody (1:100 dilution in PBS/BSA 0.1%), and then incubated for 30 minutes with the DAKO Envision System and 5 minutes with DAB. The immunocytochemical reactions were observed using a light microscope. Pictures were taken at 100× objective magnifications. For immunofluorescence, cells were incubated overnight in a wet chamber at 4° C. with anti-AKAP 4 primary antibody (1:100 dilution in PBS/BSA 0.1%) and with PE conjugated anti-mouse secondary antibody (1:500 dilution) (Abcam, Cambridge, Mass., USA). Results were analyzed by inverted fluorescence microscopy and analyzed by Flowview software.

SDS-PAGE and Western blot. Protein extracts were run in a denaturing polyacrylamide gel (SDS-PAGE) as follows: 2 μg of protein was diluted in 10 μL RIP A buffer (20 mM Tris-HCl pH 7.5, 150 mM NaCl, 1 mM Na2EDTA, 1 mM EGTA, 1% NP-40, 1% sodium deoxycholate, 2.5 mM sodium pyrophosphate, 1 mM beta-glycerophosphate, 1 mM Na3VO4, 1 μg/ml leupeptin) (Cell Signaling Technology, Inc. Danvers, Mass., USA), mixed with 10 μL Laemmli sample buffer (4% SDS, 20% glycerol, 10% 2-mercaptoethanol, 0.004% bromphenol blue and 0.125 M Tris HCl, pH 6.8) (Sigma-Aldrich, Inc., 63103 St. Louis, Mo., USA) and heated at 95° C. for 5 minutes. Samples were resolved through a 12% acrylamide minigel (Bio-Rad Laboratories, Inc. Hercules, Calif., USA) and electro-blotted on a PVDF membrane (150 mA, o/n at 4° C.) in transfer buffer (25 mM Tris, 192 mM glycine, pH 8.3, supplemented with 20% v/v methanol). After transfer, blotted proteins were displayed through Ponceau S staining (Sigma-Aldrich, MO, USA).

Indirect enzyme-linked immunosorbent assay (ELISA) to detect circulating anti-AKAP-4 lgG. An ELISA was performed on the sera of 15 prostate cancer patients and 7 healthy patients with no known abnormalities. Polystyrene 96-well flat-bottom plates were coated with AKAP-4 recombinant protein (5 μg/μl) and incubated overnight at 4° C. After washing and blocking with SUPERBLOCK® buffer (Pierce, Rockford, Ill., USA), plates were placed at 37° C. for 2 hours. Each sample, as well as the negative controls (PBS/FBS), were diluted 1:1000 in SUPERBLOCK® buffer and incubated for 4 hours at room temperature. After washing with PBS/0.05% Tween-20, horseradish peroxidase conjugated goat anti-human IgG (Pierce), diluted 1:5000 in SUPER-BLOCK®, was added an allowed to incubate at room temperature for 2 hours. Next, the 1-Step Ultra TMB-ELISA chromogenic substrate (Pierce) was added to each well for color development for 10 minutes. After blocking the reaction with sulfuric acid, the intensity was measured by the Victor-2 microplate multi-label counter (PerkinElmer, Waltham, Mass., USA) at 450 nm. All samples were run in triplicate.

Isolation of peripheral blood mononuclear cells (PBMC) and generation of dendritic cells. By separation of heparinized blood with density gradient centrifugation performed with FicoiiHypaque, we separated PBMC from 6 prostate cancer patients. PBMC were seeded into 6-well culture plates with 3 ml RPMI 1640 and 10% fetal bovine serum (FBS) at 8-10×106 cells per well. After 2 hours at 37° C. and 5% CO2, we removed the non-adherent cells and cultured the adherent cells in RPMI 1640 supplemented with 10% FBS, 1000 IU/ml interleukin 4 (IL-4) and 800 IU/ml granulocyte-macrophage colony-stimulating factor (GM-CSF). After a week of culture, DC were harvested for pulsing with AKAP-4 protein (37).

DC pulsing. DC were washed twice and transferred to a 50 mL polypropylene tube. Recombinant AKAP-4 was mixed with the cationic lipid DOTAP (Roche, Mannheim, Germany) (38) at room temperature for 20 minutes, and added to the DC for 3 hours at 37° C., with occasional agitation.

In vitro generation of AKAP-4-specific CTL. Antigen pulsed DC were added in the culture with fresh autologous PBMCs at a ratio of 1:10 in RPMI 1640 with 10% autologous serum, 10 IU/ml IL-2 and 5 ng/ml IL-7. These cells were co-cultured at 37° C., 5% CO2. Irradiated autologous PBMC feeder cells and AKAP-4 protein (50 μg/ml) were added every 7 days for two weeks, and IL-2 was added every 3 days (23).

Cytotoxicity assay. Standard 4 hour 51 Cr-release assays were performed to evaluate cytotoxic responses from the AKAP-4-stimulated PBMCs. Target cells included autologous DC with and without AKAP-4, and biopsy-isolated epithelial prostate tumor cells (at the effector-target cell ratios of 40:1, 20:1 or 5:1). Antibodies against HLA class I (W6/32) and HLA class II (L243) were added at a concentration of 25 μg/ml to evaluate HLA-restricted cytotoxicity, with a fixed 20:1 effector:target ratio. Standard deviations were determined on the results of the runs in triplicates (37).

ELISA for T cell cytokine expression. ELISA was performed on the supernatants of activated PBMCs following 4-hour co-culture with autologous tumor cells (20:1 T cell to tumor cell ratio). The U-CyTech sandwich ELISA kits (U-CyTech, Utrecht, The Netherlands) were used for the detection of human IL-4, IL-5, IL-10, IFN-γ and TNF-α, following the manufacturer's directions. Reactions were developed by adding TMB Microwell substrate, stopping the reaction by addition of 2M H2SO4, then reading the absorbance at 450 nm.

ELISPOT analysis for the measurement of IFN-y. IFN-y expression by patients' PBMCs cocultured with autologous prostate cancer cells (20:1 lymphocyte to tumor cell ratio) was evaluated using ELISPOT assay (U-CyTech, Utrecht, The Netherlands), according to manufacturer's directions. Briefly, 96-well plates (Millipore, Bedford, Mass.) were coated with 100 μL diluted anti-IFN-y antibody. After overnight incubation at 4° C., plates were washed with PBS and blocked with provided buffer. PBMCs were added in triplicate and incubated with 20 μg/ml AKAP-4 protein at 37° C. in 5% CO2 for 48 hours. Plates were then washed extensively (10 times) and incubated overnight with 100 μl biotinylated detection antibodies at 4° C. After washing 6 times, 50 μl diluted GABA were added and incubated for 1 hour at 37° C. Plates were then washed twice and spots were developed by adding 30 μL Activator solution and incubating at room temperature for 25-30 minutes. Spots counts were performed with an AID ELISPOT Reader System (Cell Technology, Inc., Columbia, Md., USA).

Figure 1:
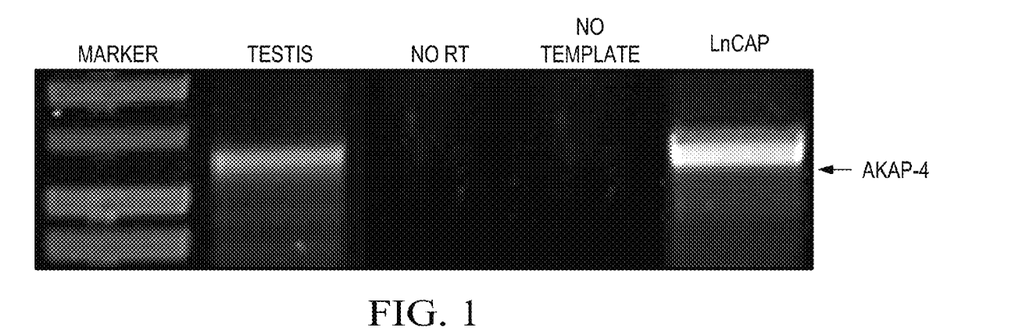
FIG. 1 is an image showing the AKAP-4 expression at the RNA level was investigated by RT-PCR in normal testis (positive control) and LnCAP cells.
Figure 2A:
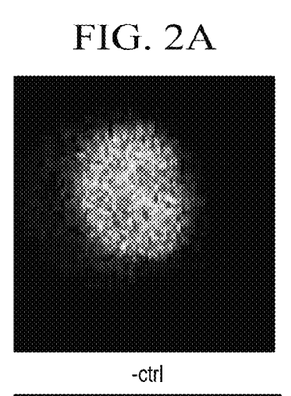
FIGS. 2a-2f are images of cells showing the representative IF and ICC performed on the LnCAP cell line.
Figure 2B:
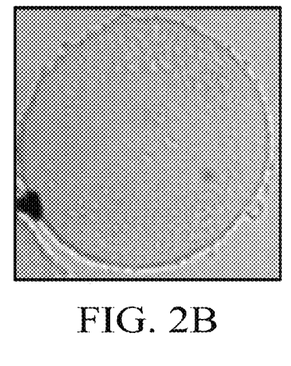
Figure 2C:
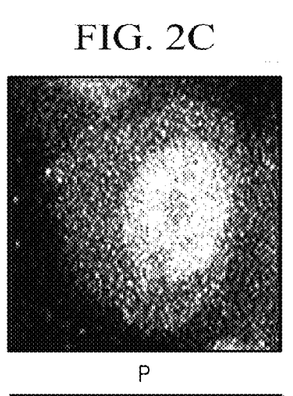
Figure 2D:
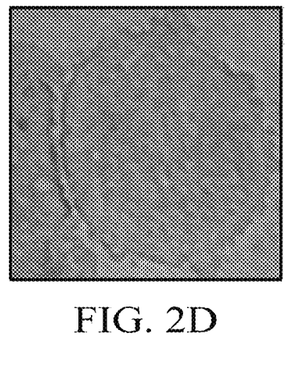
Figure 2E:
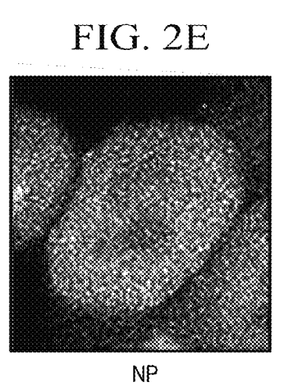
Figure 2F:
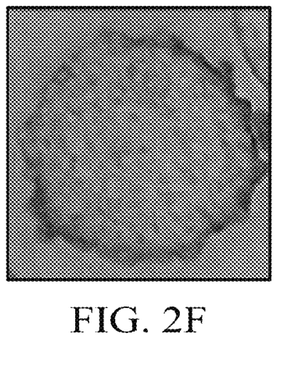
Figure 3A:
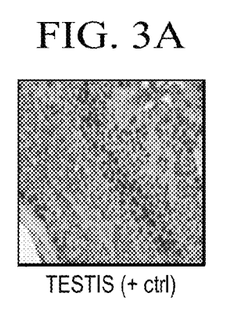
FIGS. 3a-3h are images of prostate cancer biopsies by IHC with anti-AKAP-4 antibody.
Figure 3B:
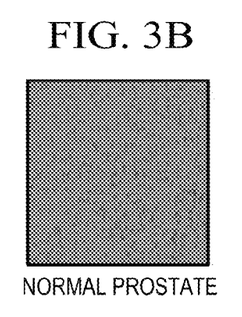
Figure 3C:
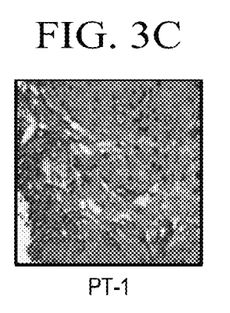
Figure 3D:
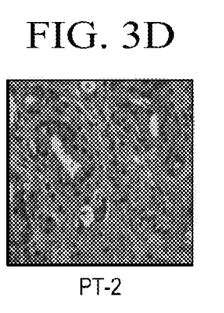
Figure 3E:
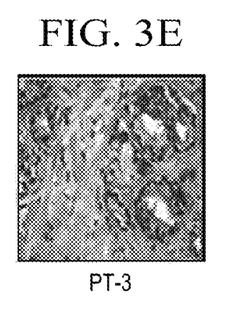
Figure 3F:
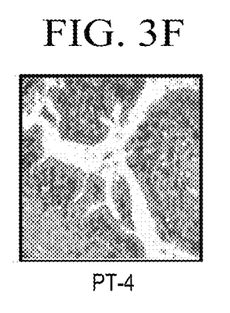
Figure 3G:
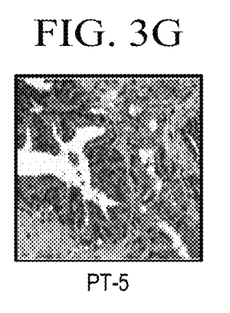
Figure 3H:
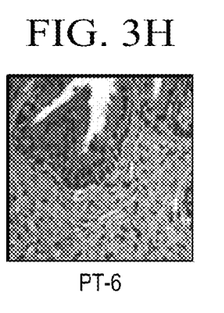

FIG. 1 is an image showing the AKAP-4 expression at the RNA level was investigated by RT-PCR in normal testis (positive control) and LnCAP cells. Unspecific band generation was ruled out by the lack of amplification in the absence of template, while lack of a positive band in PCR reaction with non-reverse transcribed RNA (No RT) assured no amplification of genomic DNA. AKAP-4 gene is aberrantly expressed by the LnCAP prostate cancer cell line.

AKAP-4 expression was tested at the mRNA level in the human prostate cancer cell line LnCAP using mRNA from normal test is as positive control for a RT-PCR assay. A positive band of the expected size was detected in testis- and LnCAP-derived cDNA. Absence of PCR product in reactions performed with LnCAP RNA without reverse transcription ruled out the possibility of genomic DNA contamination. PCR run with water in place of cDNA served as a negative control.

FIGS. 2a-2f are images of cells showing the representative IF and ICC performed on the LnCAP cell line. Permeabilized (P) and non-permeabilized (NP) cells show the positive stain by the AKAP-4 monoclonal antibody (green FITC stain for IF and brown DAB stain for ICC). Blue stain (DAPI) revealed cell nuclei. Pictures taken without the specific anti-AKAP-4 antibody served as negative control (-ctrl). AKAP-4 protein expression in the cytoplasm and cell membrane of LnCAP cells. The presence of AKAP-4 protein was tested in the cytoplasm and at the surface of LnCAP cells by immunocytochemistry techniques. FIGS. 2a-2f displays representative pictures taken by fluorescence or by light microscopy. Under fluorescent microcopy, AKAP-4 is seen as a green signal, or by the 3,3'-Diaminobenzidine (DAB) brown signal under white light. Both analyses were performed with non-permeabilized (NP) cells to show surface AKAP-4 expression, or with permeabilized (P) cells to display cytoplasmic localization.

FIGS. 3a-3h are images of prostate cancer biopsies by IHC with anti-AKAP-4 antibody. Positive signal is given by DAB brown stain; tissues were counter-stained with hematoxylin. Normal prostate was used as negative control (no AKAP-4 signal), while tissue taken from normal testis was the positive control (+Ctrl). Patient #4 did not express AKAP-4. AKAP-4 protein is detectable in human PC biopsies by immunohistochemistry. AKAP-4 expression in LnCAP tumor cells prompted a test to determine its presence in primary tumor samples derived from human PC biopsies. FIGS. 3a-3h display representative pictures of immunohistochemistry assays for the detection of AKAP-4 protein: results showed AKAP-4 positive brown signal in 13 out of 20 analyzed cases; patient number 4 (PT4), negative for AKAP-4, is also shown. Normal testis tissue was used as a positive control. The absence of a positive signal in 20 analyzed normal prostate samples confirmed the selectively of AKAP-4 expression in neoplastic prostate tissue only (data not shown).

Figure 4A:
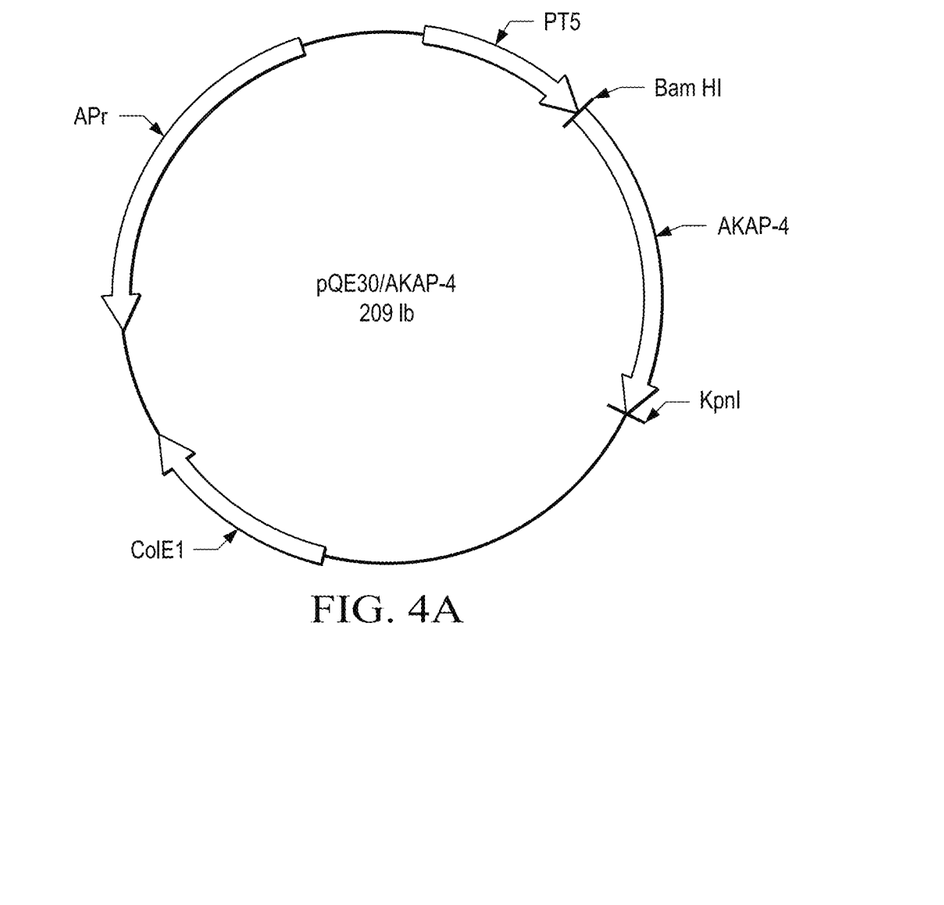
FIGS. 4a and 4b are images of the generation of recombinant human AKAP-4 protein.
Figure 4B:
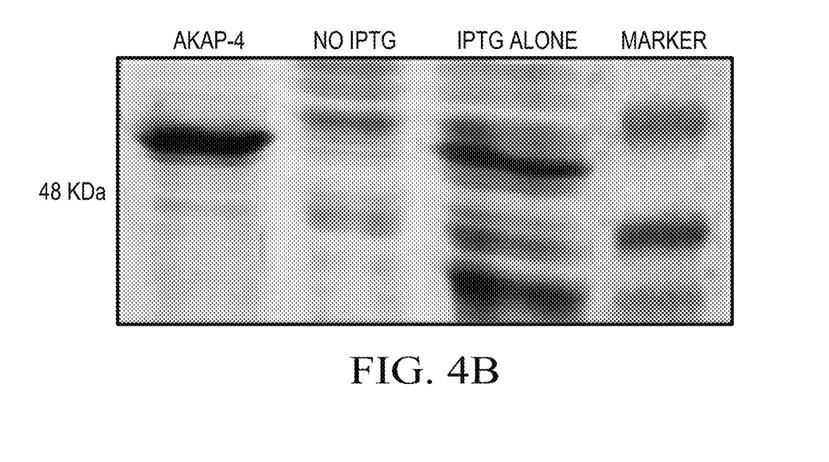

FIGS. 4a and 4b are images of the generation of recombinant human AKAP-4 protein. FIG. 4a is an image of the AKAP-4 generated through the PQE30 plasmid subcloned into M15 E. coli cells. Protein purification was confirmed by SDS-PAGE. FIG. 4b is an image of the purified protein elution fraction in the presence of the expression inducer IPTG resulted in a single band of 48 KDa (AKAP-4), while in the absence of IPTG (No IPTG) or in the absence of PQE30/AKAP-4 plasmid (IPTG alone) no single band was detected.

Generation of recombinant human AKAP-4 protein. Ectopic AKAP-4 expression in PC primary samples prompted the evaluation of its immunogenicity through ELISA and cytotoxicity assays. To this goal, recombinant AKAP-4 protein was produced by molecular biology techniques. FIG. 4a shows the expression vector used to produce human AKAP-4 in E. coli, according to an efficient procedure described elsewhere for the generation of human recombinant PTTG-1 and SP17 proteins (16, 37). 6His-tagged AKAP-4 protein was isolated using commercial Ni-based resins as detailed in the Materials and Methods section; FIG. 4b shows the SDS-PAGE resolved proteins obtained from E. coli transformed with AKAP-4 expression plasmid cultured in the presence (AKAP-4) or in the absence (no IPTG) of the expression inductor IPTG. Also tested were proteins isolated from the same E. coli strain transformed with an empty expression vector and cultured in the presence of IPTG (IPTG alone). SDS-PAGE results confirmed specific human AKAP-4 generation and isolation, since a band of the expected molecular weight was produced only by bacteria transformed with AKAP-4 expression plasmid in the presence of IPTG but not in any other culture condition tested (FIG. 4b). Isolated AKAP-4 protein was endotoxin-free, as measured by the Endotoxin Colorimetric Assay Kit, HEK-BLUE™ (InvivoGen) (data not shown).

Figure 5:
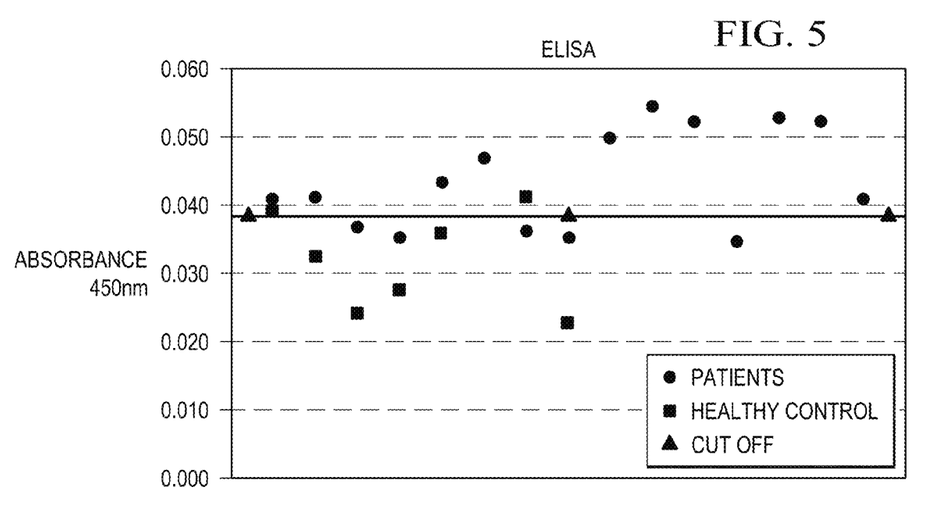
FIG. 5 is a plot of the indirect ELISA performed on serum from 15 prostate cancer patients and 7 healthy subjects with no known abnormalities to detect circulating anti-AKAP-4 specific antibodies.

FIG. 5 is a plot of the indirect ELISA performed on serum from 15 PC patients and 7 healthy subjects with no known abnormalities to detect circulating anti-AKAP-4 specific antibodies. The cut-off point (mean+3 STDEV), based on healthy controls' values, is OD450 nm=0.038. Representative samples are shown. Detection of specific anti-AKAP-4 antibodies in PC patients' serum. The presence of anti-AKAP-4 immunoglobulins in the serum of 15 PC patients was shown by indirect ELISA with recombinant AKAP-4. Ten patients tested positive for circulating anti-AKAP-4 antibodies, as shown by absorbance levels above the cut-off point, based on healthy control values (mean+3 standard deviations).

Figure 6:
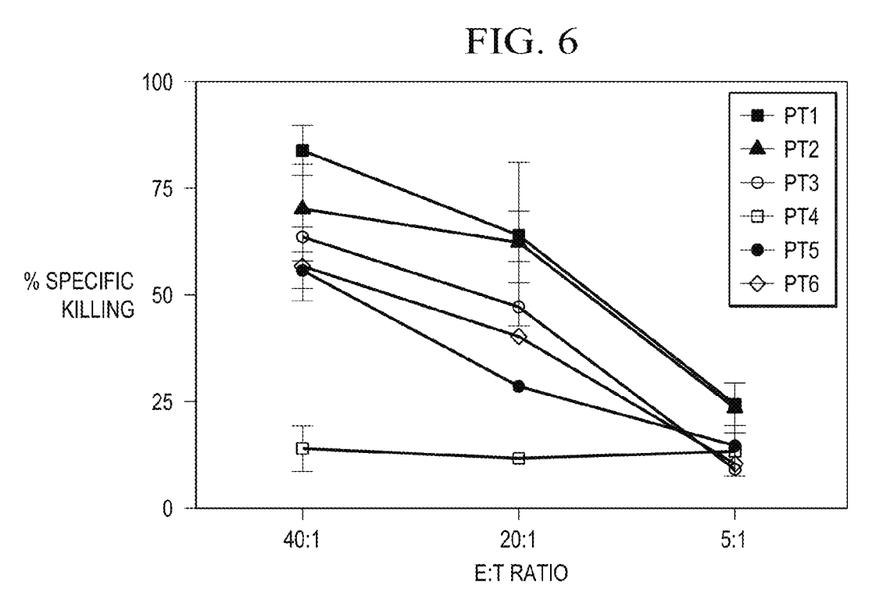
FIG. 6 is a plot of the in vitro cytotoxicity assay.
Figure 7A:
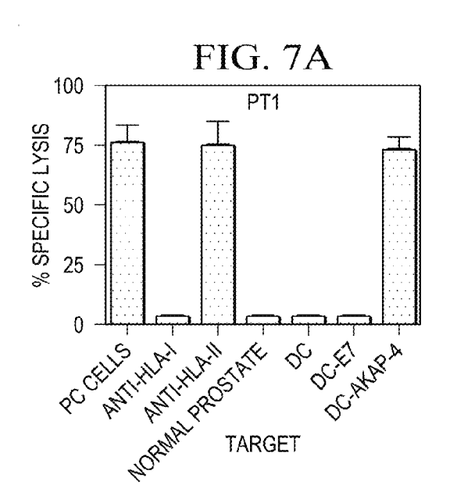
FIGS. 7a-7f are plots of In vitro cytotoxicity assay was performed at the fixed E:T ratio of 20:1 using Destimulated responder T cells as effectors against the indicated targets.
Figure 7B:
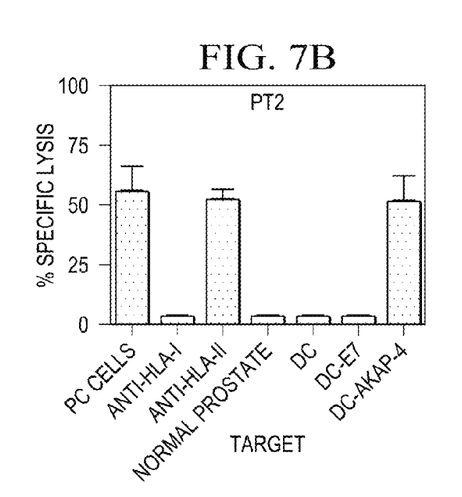
Figure 7C:
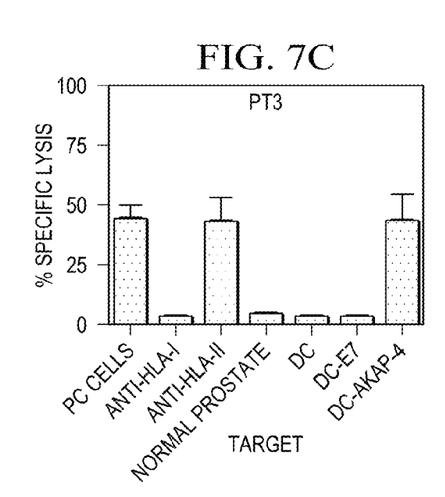
Figure 7D:
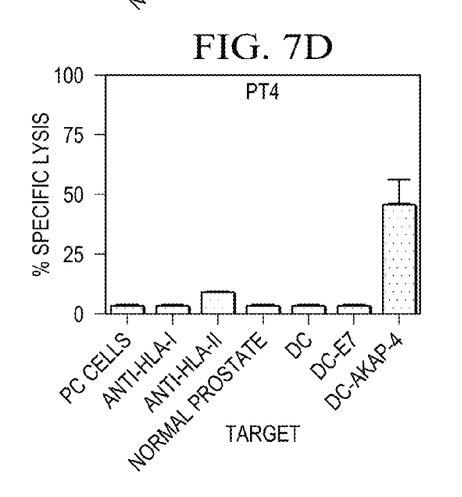
Figure 7E:
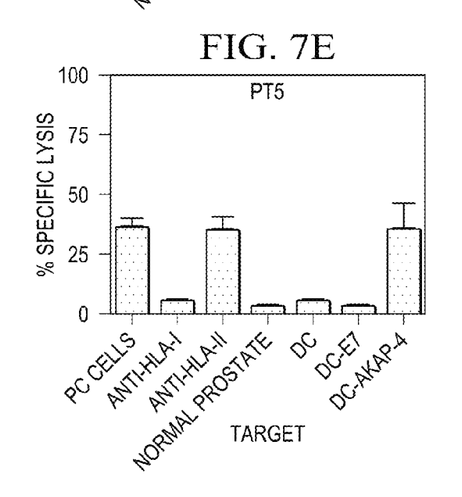
Figure 7F:
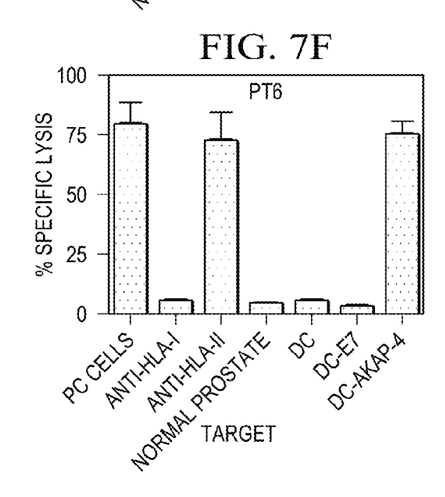

FIG. 6 is a plot of the In vitro cytotoxicity assay. Following stimulation of PBMC with AKAP-4-loaded DC, responder T cells (effector cells) were co-cultured with autologous PC cells (target cells) for 6 hours. Percentage of specific lysis was determined through a standard 51 Cr-release assay. Error bars indicate 95% C. I. with 0=0.05, as determined from the results of triplicate experiments. The X-axis displays effector:target (E:T) ratios. No significant cytotoxic response was detected in patient #4, which accords with the absence of AKAP-4 expression by tumor cells as determined by immunohistochemistry (see FIGS. 3a-3h). In vitro CTL responses. Following stimulation of PBMC with AKAP-4 loaded DC, the ability of T cells from 6 PC patients to kill autologous PC cells was tested through a standard in vitro 51Cr-release cytotoxicity assay. FIG. 6 shows that stimulation with AKAP-4-presenting DC triggered CTL activity against AKAP-4 positive autologous PC cells, even at low effector:target ratios (40:1 and 20:1). No significant lysis was observed in cells derived from patient #4, in accordance with lack of AKAP-4 expression shown by immunohistochemistry (FIGS. 3a-3h).

FIGS. 7a-7f are plots of In vitro cytotoxicity assay performed at the fixed E:T ratio of 20:1 using Destimulated responder T cells as effectors against the indicated targets. The assay was run in triplicate, and error bars indicate 95% C.I. with a=0.05. To determine HLA-restriction of CTL response, specific lysis of autologous PC cells was measured in the presence of HLA class I or HLA class 11-specific blocking antibodies (Anti-HLA-I and Anti-HLA-II, respectively). To evaluate AKAP-4 specificity, specific lysis was measured of normal prostate cells (AKAP-4 negative), untreated DC or DC loaded with unrelated antigen E7 (DC-E7) or DC loaded with AKAP-4 (DCAKAP-4). To test the specificity and the HLA-restriction of the evidenced cytotoxic effect, a 51Cr-release assay was performed using HLA class I or HLA class II blocking antibodies and different target cells, namely PC cells, normal epithelial prostate cells, autologous DC unmodified or loaded with AKAP-4 or HPV antigen E-7 (FIGS. 7a-7f). Patient 4 T cells were active against AKAP-4 presenting DC only, while they did not recognize targets lacking AKAP-4 expression. Results indicate that the cytotoxic activity was HLA-1 restricted, as HLA class I (but not HLA class II) blocking markedly reduced PC cell lysis (for all patients except #4, two-tailed t-test, p<0.001). AKAP-4 specificity was confirmed by lack of activity against patient #4 PC cells, (which are AKAP-4 negative) and, in all other patients, against AKAP-4 negative targets, namely normal prostate epithelial cells and unmodified or unrelated antigen E-7-loaded autologous DC.

Figure 8A:
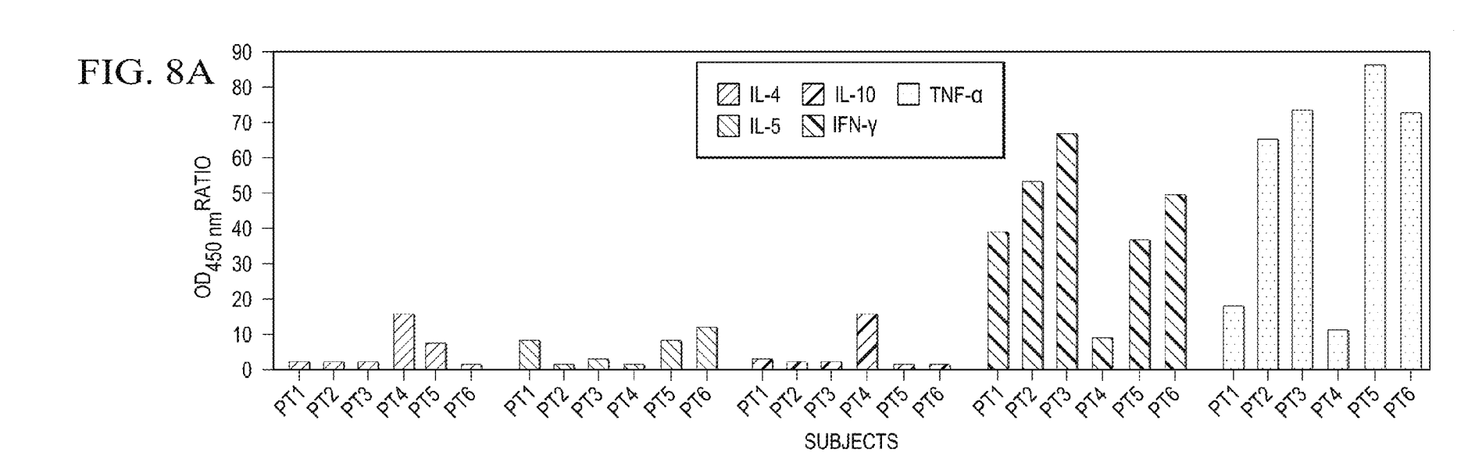
FIGS. 8a and 8b are graphs of the results for each patient.
Figure 8B:
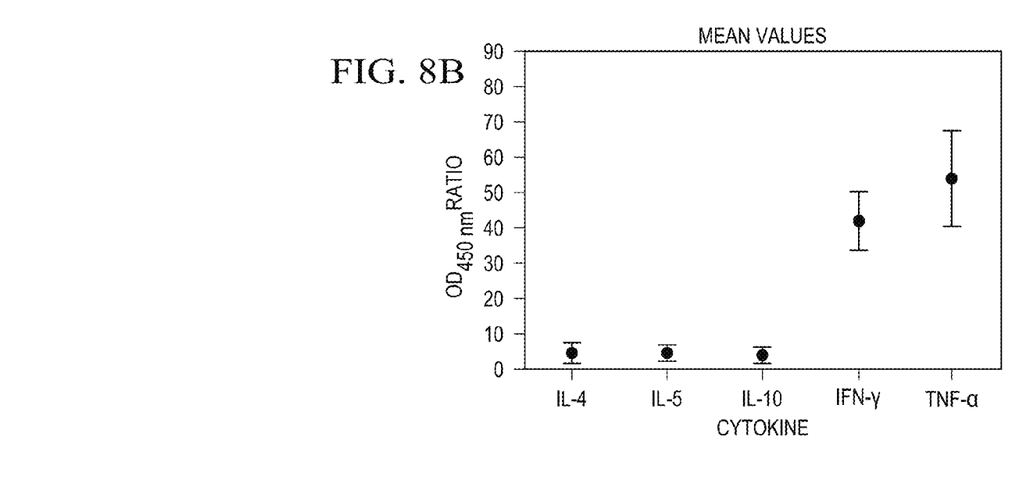

FIG. 8A is a graph of the results for each patient. An ELISA for the measurement of IL-4, IL-5, IL-1 0, IFN-y and TNF-α in the conditioned media of responder T cells co-cultured with autologous PC cells isolated from biopsies or with autologous E7-loaded DC as negative controls. Mean optical densities (OD 450 nm) were calculated from experiments run in triplicate. OD ratios were obtained dividing OD values derived from T cell/PC co-cultures by the values derived from T cell/control DC co-cultures. FIG. 8B is a graph of the mean values of all patients are shown, with error bars indicating 95% C. I. with α=0.05.

Cytokine expression by in vitro-generated AKAP-4-specific CTL. To evaluate the cytokine profile of DC-stimulated AKAP-4-specific T cells, the mean OD450 nm displayed by supernatants following co-culture with AKAP-4 positive PC cells was divided by the mean OD 450 nm displayed following co-culture with AKAP-4 negative and E7 positive autologous DC. FIG. 8a shows the OD 450 nm ratios calculated for IL-4, IL-5, IL-1 0, IFN-y and TNF-α for each patient, and FIG. 8b shows the mean values of all subjects under study: compared with HPV E7 protein loaded DC, AKAP-4 positive PC cells induced a reduction or an insignificant increment (less than 8 times) of IL-4, IL-5 and IL-10 secretion by T cells, and a marked increase in IFN-y and TNF-α production (from 40 to 85 times). Only a slight IFN-y and TN F-α increase (less than 10 times) was detectable from patient #4 T cells following co-culture with autologous AKAP-4 negative PC cells. The apparent Th1 cytokine profile IFN-y-secreting lymphocyte profile was further confirmed by ELISPOT enumeration of IFN-expressing T cells following co-culture with autologous PC cells.

Figure 9:
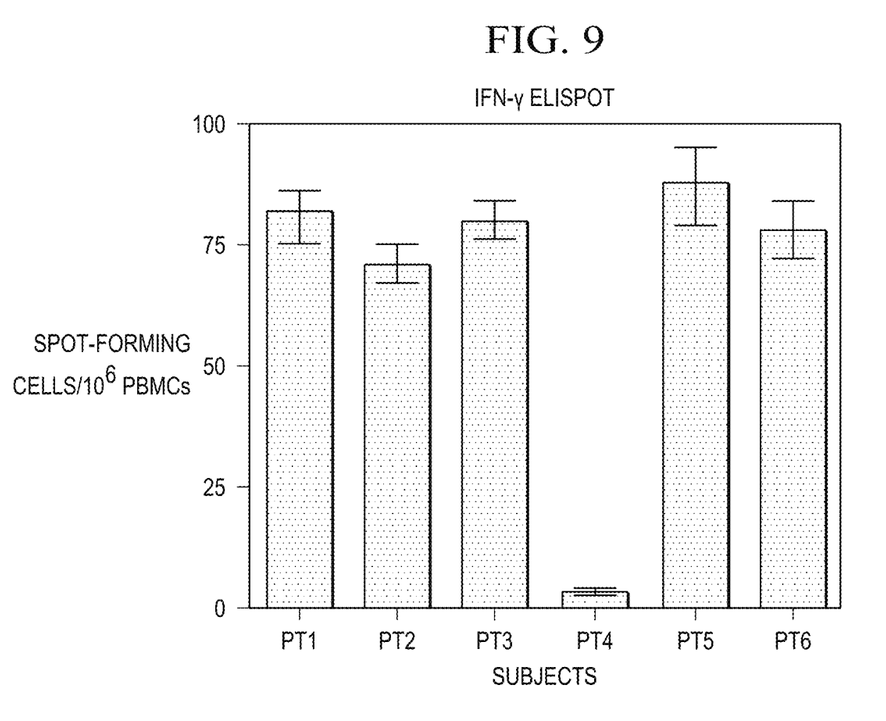
FIG. 9 is a histogram showing the mean values calculated from experiments run in triplicate for each patient.

FIG. 9 is a histogram showing the mean values calculated from experiments run in triplicate for each patient. Error bars indicate 95% C.I. with 0=0.05. Following co-culture with autologous PC cells, DC-primed responder T cells were harvested and analyzed by the ELISPOT assay for IFN-y expression. FIG. 9 displays the mean spot-forming cells per 106 T cells, as calculated from assays run in triplicate for each patient. Co-culture with AKAP-4 negative PC cells from patient #4 induced a significantly lower number of IFN-y producing cells compared with all other subjects (two-tailed t-test p<0.001 for PT4 versus all other patients).

CTA are an expanding family of tumor-associated antigens particularly suitable for tumor immunotherapy because of their highly tumor restricted expression pattern and their immunogenicity (11, 16, 17, 23, 28, 31, 37, 39). The aberrantly expressed CTA, AKAP-4, was identified as in multiple myeloma primary cells, showing the possibility to exploit AKAP-4 as a tumor biomarker by detecting specific anti-AKAP-4 immunoglobulins in patients' serum (31); interestingly, this innovative result also showed that AKAP-4 was immunogenic in vivo (31). AKAP-13, another member of the PKA anchor protein family, has been shown to interact with the PC biomarker tissue transglutaminase in tumor cells (40). AKAP-4 expression in the PC cell line LnCAP was examined and found that AKAP-4 was present at the mRNA and protein level. AKAP-4 protein was localized both in the cytoplasm and at the surface of LnCAP cells, as shown by immunocytochemistry assays.

AKAP-4 expression in PC biopsies was analyzed from 15 patients and 7 healthy subjects that underwent prostate biopsies for diagnostic purposes but without any known abnormalities. Immunohistochemistry assays gave evidence of aberrant AKAP-4 expression in the prostate epithelial cells from 13 patients but not from healthy subjects. Overall, the analysis showed a 65% incidence of AKAP-4 expression in PC patients. Average AKAP-4 levels were higher than in normal testis, used as positive control (17, 31, 41, 42). AKAP-4 could contribute to the invasiveness of PC tumor cells, as it interacts with PKA, that has been shown to mediate calcitonin-induced PC invasive potential in vitro (32).

The ability to elicit spontaneous immune response, often resulting in the production of specific circulating antibodies, is thought to be a fundamental prerequisite for tumor antigens to be exploitable as immunotherapy targets in different tumors, including prostate cancer (25, 43-47). An indirect ELISA demonstrated the presence of circulating antiAKAP-4 immunoglobulins in patients' sera. AKAP-4 and another CTA, SP17 were identified as multiple myeloma-associated antigens, showing similar results (31, 37).

Spontaneous generation of anti-AKAP-4 antibodies indicated the presence of naturally rising but ineffective AKAP-4-directed immune-surveillance against PC. Using autologous DC presenting recombinant AKAP-4 protein, the stimulated PBMCs were isolated from the patients' blood through a technique previously used to successfully generate cytotoxic lymphocytes against the CTA SP17 (17, 21-23). Cytotoxicity assays showed that AKAP-4-loaded DC stimulated T cells were able to kill autologous PC cells with high efficiency, since low effector to target ratios were needed to detect cytotoxic activity (48, 49).

Tumor immunotherapy must have efficient activity against tumor cells and high specificity to prevent autoimmune reactions (12, 22, 50). The possibility was ruled out that stimulated PBMCs could have an unspecific activity, since no cytotoxic effect was shown against AKAP-4 negative cells, namely normal prostate epithelial cells, autologous unmodified DC, or DC loaded with the prostate unrelated HPV-16 and -17 protein E7. Absence of killing activity against PC cells from a patient that tested negative for AKAP-4 further indicated the antigen specificity of the cytotoxic response.

Since HLA class I but not HLA class II blocking resulted in hampered cytotoxicity against PC cells, tumor killing was mainly mediated by CD8+ T-lymphocytes (20, 21). To better characterize the cells responsible for the cytotoxic activity against prostate cancer, the inventors assayed for expression of a panel of cytokines secreted in the culture medium of simulated T cells co-cultured with target cells: increased IFN-y and TNF-α levels, with no significant change in IL-4, IL-5 and IL-10, clearly indicated a Th1-bias (51-54). Importantly, the absence of Th1-cytokine expression by T cells derived from the AKAP-4 negative patient further supported the antigen specificity of the anti-tumor lymphocyte response. Data for IFN-y were confirmed by the ELISPOT technique.

A Th1 cytokine milieu has been shown to play a critical role in PC protection by immunotherapy in TRAMP mice (55). Notably, a phase I clinical trial recently showed that immunotherapy based on the tumor-associated antigen MUC-1 strongly augmented Th1 (IFN-y and TNF-α) but not Th2 (IL-4) cytokine expression (56). Further, the possibility to increase IFN-y but not IL-4 levels is relevant because IFN-y has been shown to enhance human CTL responses against PC cells (57) while IL-4 stimulates androgen-independent growth of the LnCAP PC cell line (58). The lack of efficient immune-surveillance in PC patients despite the high expression of a wide antigenic panel by tumor cells suggests the existence of immunomodulatory mechanisms hampering the naturally occurring antitumor immune responses (59). It will be critical to determine whether AKAP-4 specific CTLs that were generated in vitro have the ability to overcome immune tolerance in vivo, which represents a main issue in PC treatment because of high frequencies of Foxp3+ regulatory cells in PC microenvironment with low IFN-y expression and CTL activation (59-61).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Ferlay J, Autier P, Boniol M, Heanue M, Colombet M, Boyle P. Estimates of the cancer incidence and mortality in Europe in 2006. Ann Oncol 2007; 18(3):581-592.
2. Leman E S, Getzenberg R H. Biomarkers for prostate cancer. J Cell Biochem 2009; 108(1):3-9.
3. Ferro M A, Barnes I, Roberts J B, Smith P J. Tumour markers in prostatic carcinoma. A comparison of prostate-specific antigen with acid phosphatase. Br J Urol 1987; 60(1):69-73.
4. Constantinou J, Feneley M R. PSA testing: an evolving relationship with prostate cancer screening. Prostate Cancer Prostatic Dis 2006; 9(1):6-13.
5. Barry M J. Clinical practice. Prostate-specific-antigen testing for early diagnosis of prostate cancer. N Engl J Med 2001; 344(18):1373-1377.
6. Thompson I M, Pauler O K, Goodman P J, Tangen C M, Lucia M S, Parnes H L, Minasian L M, Ford L G, Lippman S M, Crawford E D, Crowley J J, Coltman C A, Jr. Prevalence of prostate cancer among men with a prostate-specific antigen level < or =4.0 ng per milliliter. N Engl J Med 2004; 350(22):2239-2246.
7. Drake C G. Prostate cancer as a model for tumour immunotherapy. Nat Rev Immunol 2010; 10(8):580-593.
8. World's first cancer vaccine licensed: PROVENGE(®). Hum Vaccin 2010; 6:6.
9. Chiriva-Internati M, Grizzi F, Wachtel M S, Jenkins M, Ferrari R, Cobos E, Frezza E E. Biological treatment for liver tumor and new potential biomarkers. Dig Dis Sci 2008; 53(3):836-843.
10. Chiriva-Internati M, Grizzi F, Weidanz J A, Ferrari R, Yuefei Y, Velez B, Shearer M H, Lowe D B, Frezza E E, Cobos E, Kast W M, Kennedy R C. A NOD/SCID tumor model for human ovarian cancer that allows tracking of tumor progression through the biomarker Sp17. J Immunol Methods 2007; 321 (1-2):86-93.
11. Straughn J M, Jr., Shaw D R, Guerrero A, Bhoola S M, Racelis A, Wang Z, ChirivaInternati M, Grizzle W E, Alvarez R D, Lim S H, Strong T V. Expression of sperm protein 17 (Sp17) in ovarian cancer. Int J Cancer 2004; 108(6):805-811.
12. Dannull J, Diener P A, Prikler L, Furstenberger G, Cerny T, Schmid U, Ackermann O K, Groettrup M. Prostate stem cell antigen is a promising candidate for immunotherapy of advanced prostate cancer. Cancer Res 2000; 60(19):5522-5528.
13. Harada M, Kobayashi K, Matsueda S, Nakagawa M, Noguchi M, ltoh K. Prostatespecific antigen-derived epitopes capable of inducing cellular and humoral responses in HLA-A24+ prostate cancer patients. Prostate 2003; 57(2):152-159.
14. Lu J, Celis E. Recognition of prostate tumor cells by cytotoxic T lymphocytes specific for prostate-specific membrane antigen. Cancer Res 2002; 62(20):5807-5812.
15. Peshwa M V, Shi J D, Ruegg C, Laus R, van Schooten W C. Induction of prostate tumorspecific CD8+ cytotoxic T-lymphocytes in vitro using antigen-presenting cells pulsed with prostatic acid phosphatase peptide. Prostate 1998; 36(2):129-138.
16. Chiriva-lnternati M, Ferrari R, Prabhakar M, Yu Y, Baggoni L, Moreno J, Gagliano N, Portinaro N, Jenkins M R, Frezza E E, Hardwicke F, D'Cunha N, Kast W, Cobos E. The pituitary tumor transforming gene 1 (PTTG-1): an immunological target for multiple myeloma. J Transl Med 2008; 6:15.
17. Chiriva-lnternati M, Weidanz J A, Yu Y, Frezza E E, Jenkins M R, Kennedy R C, Cobos E, Kast W M. Sperm protein 17 is a suitable target for adoptive T-cell-based immunotherapy in human ovarian cancer. J Immunother 2008; 31(8):693-703.
18. Gray A, Raft A B, Chiriva-lnternati M, Chen S Y, Kast W M. A paradigm shift in therapeutic vaccination of cancer patients: the need to apply therapeutic vaccination strategies in the preventive setting. Immunol Rev 2008; 222: 316-327.
19. Yu Y, Pilgrim P, Zhou W, Gagliano N, Frezza E E, Jenkins M, Weidanz J A, Lustgarten J, Cannon M, Bumm K, Cobos E, Kast W M, Chiriva-Internati M. rAAV/Her-2/neu loading of dendritic cells for a potent cellular-mediated MHC class I restricted immune response against ovarian cancer. Viral Immunol 2008; 21 (4):435-442.
20. Chiriva-lnternati M, Wang Z, Pochopien S, Salati E, Lim S H. Identification of a sperm protein 17 CTL epitope restricted by HLA-A 1. Int J Cancer 2003; 107(5):863-865.
21. Chiriva-lnternati M, Wang Z, Salati E, Wroblewski D, Lim S H. Successful generation of sperm protein 17 (Sp17)-specific cytotoxic T lymphocytes from normal donors: implication for tumour-specific adoptive immunotherapy following allogeneic stem cell transplantation for Sp17-positive multiple myeloma. Scand J Immunol 2002; 56(4):429-433.
22. Chiriva-lnternati M, Wang Z, Xue Y, Bumm K, Hahn A B, Lim S H. Sperm protein 17 (Sp17) in multiple myeloma: opportunity for myeloma-specific donor T cell infusion to enhance graft-versus-myeloma effect without increasing graft-versus-host disease risk. Eur J Immunol 2001; 31 (8):2277-2283.
23. Lim S H, Wang Z, Chiriva-lnternati M, Xue Y. Sperm protein 17 is a novel cancer-testis antigen in multiple myeloma. Blood 2001; 97(5):1508-1510.
24. Fossa A, Alsoe L, Crameri R, Funderud S, Gaudernack G, Smeland E B. Serological cloning of cancer/testis antigens expressed in prostate cancer using eDNA phage surface display. Cancer ImmunolImmunother 2004; 53(5):431-438.

25. Fossa A, Berner A, Fossa S O, Herres E, Gaudernack G, Smeland E B. NY-ES0-1 protein expression and humoral immune responses in prostate cancer. Prostate 2004; 59(4): 440-447.
26. Parmigiani R B, Bettoni F, Vibranovski M D, Lopes M H, Martins W K, Cunha I W, Soares F A, Simpson A J, de Souza S J, Camargo A A. Characterization of a cancer/testis (CT) antigen gene family capable of eliciting humoral response in cancer patients. Proc Natl Acad Sci USA 2006; 103(48):18066-18071.
27. Sampson N, Untergasser G, Lilg C, Tadic L, Plas E, Berger P. GAGEC1, a cancer/testis associated antigen family member, is a target of TGF-beta1 in age-related prostatic disease. Mech Ageing Dev 2007; 128(1):64-66.
28. Scanlan M J, Simpson A J, Old L J. The cancer/testis genes: review, standardization, and commentary. Cancer Immun 2004; 4:1.
29. Jin J, Smith F D, Stark C, Wells C D, Fawcett J P, Kulkarni S, Metalnikov P, O'Donnell P, Taylor P, Taylor L, Zougman A, Woodgett J R, Langeberg L K, Scott J D, Pawson T. Proteomic, functional, and domain-based analysis of in vivo 14-3-3 binding proteins involved in cytoskeletal regulation and cellular organization. Curr Bioi 2004; 14(16): 1436-1450.
30. Turner R M, Musse M P, Mandai A, Klotz K, Jayes F C, Herr J C, Gerton G L, Moss S B, Chemes H E. Molecular genetic analysis of two human sperm fibrous sheath proteins, AKAP4 and AKAP3, in men with dysplasia of the fibrous sheath. J Androl 2001; 22(2):302-315.
31. Chiriva-lnternati M, Ferrari R, Yu Y, Hamrick C, Gagliano N, Grizzi F, Frezza E, Jenkins M R, Hardwick F, D'Cunha N, Kast W M, Cobos E. AKAP-4: a novel cancer testis antigen for multiple myeloma. Br J Haematol 2008; 140(4):465-468.
32. Sabbisetti V S, Chirugupati S, Thomas S, Vaidya K S, Reardon D, Chiriva-Internati M, Iczkowski K A, Shah G V. Calcitonin increases invasiveness of prostate cancer cells: role for cyclic AMP-dependent protein kinase A in calcitonin action. Int J Cancer 2005; 117(4):551-560.
33. Pitkanen-Arsiola T, Tillman J E, Gu G, Yuan J, Roberts R L, Wantroba M, Coetzee G A, Cookson M S, Kasper S. Androgen and anti-androgen treatment modulates androgen receptor activity and DJ-1 stability. Prostate 2006; 66(11):1177-1193.
34. Hayward S, Cox S, Mitchell I, Hallowes R, Deshpande N, Towler J. The effects of interferons on the activity of alpha-glycerolphosphate dehydrogenase in benign prostatic hyperplasia cells in primary culture. J Urol 1987; 138(3): 648-653.
35. Yang J S, Kim H J, Ryu Y H, Yun C H, Chung O K, Han S H. Endotoxin contamination in commercially available pokeweed mitogen contributes to the activation of murine macrophages and human dendritic cell maturation. Clin Vaccine Immunol 2006; 13(3):309-313.
36. Grizzi F, Gaetani P, Franceschini B, Di leva A, Colombo P, Ceva-Grimaldi G, Bollati A, Frezza E E, Cobos E, Rodriguez y Baena R, Dioguardi N, Chiriva-lnternati M. Sperm protein 17 is expressed in human nervous system tumours. BMC Cancer 2006; 6:23.
37. Chiriva-lnternati M, Wang Z, Salati E, Bumm K, Barlogie B, Lim S H. Sperm protein 17 (Sp17) is a suitable target for immunotherapy of multiple myeloma. Blood 2002; 100(3):961-965.
38. Santin A D, Hermonat P L, Ravaggi A, Chiriva-lnternati M, Zhan D, Pecorelli S, Parham G P, Cannon M J. Induction of human papillomavirus-specific CD4(+) and CD8(+) lymphocytes by E7-pulsed autologous dendritic cells in patients with human papillomavirus type 16- and 18-positive cervical cancer. J Virol 1999; 73(7):5402-5410.
39. Chiriva-lnternati M, Cobos E, Kast W M. Advances in immunotherapy of multiplemyeloma: from the discovery of tumor-associated antigens to clinical trials. Int Rev Immunol 2007; 26(3-4): 197-222.
40. Lewis T E, Milam T O, Klingler O W, Rao P S, Jaggi M, Smith O J, Hemstreet G P, Balaji K C. Tissue transglutaminase interacts with protein kinase A anchor protein 13 in prostate cancer. Urol Oncol 2005; 23(6):407-412.
41. Kim S H, Lee S, Lee C H, Lee M K, Kim Y O, Shin D H, Choi K U, Kim J Y, Park do Y, Sol M Y. Expression of cancer-testis antigens MAGE-A3/6 and NY-ES0-1 in non-small-cell lung carcinomas and their relationship with immune cell infiltration. Lung 2009; 187(6):401-411.
42. Miles A K, Rogers A, Li G, Seth R, Powe D, McArdle S E, McCulloch T A, Bishop M C, Rees R C. Identification of a novel prostate cancer-associated tumor antigen. Prostate 2007; 67 (3):274-287.
43. McNeel D G, Nguyen L D, Storer B E, Vessella R, Lange P H, Disis M L. Antibody immunity to prostate cancer associated antigens can be detected in the serum of patients with prostate cancer. J Urol 2000; 164(5):1825-1829.
44. Korangy F, Ormandy L A, Bleck J S, Klempnauer J, Wilkens L, Manns M P, Greten T F. Spontaneous tumor-specific humoral and cellular immune responses to NY-ES0-1 in hepatocellular carcinoma. Clin Cancer Res 2004; 10(13):4332-4341.
45. Jager D, Jager E, Knuth A. Immune responses to tumour antigens: implications for antigen specific immunotherapy of cancer. J Clin Pathol 2001; 54(9):669-674.
46. Liu W M, Fowler O W, Smith P, Dalgleish A G. Pretreatment with chemotherapy can enhance the antigenicity and immunogenicity of tumours by promoting adaptive immune responses. Br J Cancer 2010; 102(1):115-123.
47. Dranoff G. Targets of protective tumor immunity. Ann NY Acad Sci 2009: 74-80.
48. Hildner K, Edelson B T, Purtha W E, Diamond M, Matsushita H, Kohyama M, Calderon B, Schraml B U, Unanue E R, Diamond M S, Schreiber R D, Murphy T L, Murphy K M. Batf3 deficiency reveals a critical role for CD8alpha+ dendritic cells in cytotoxic T cell immunity. Science 2008; 322(5904):1097-1100.
49. Zhou H, Luo Y, Mizutani M, Mizutani N, Reisfeld R A, Xiang R. T cell-mediated suppression of angiogenesis results in tumor protective immunity. Blood 2005; 106(6): 2026-2032.
50. Cha E, Fong L. Therapeutic vaccines for prostate cancer. Curr Opin Mol Ther; 12(1):77-85.
51. Chiriva-lnternati M, Liu Y, Weidanz J A, Grizzi F, You H, Zhou W, Bumm K, Barlogie B, Mehta J L, Hermonat P L. Testing recombinant adena-associated virus-gene loading of dendritic cells for generating potent cytotoxic T lymphocytes against a prototype selfantigen, multiple myeloma HM1.24. Blood 2003; 102(9):3100-3107.
52. Chiriva-lnternati M, Wang Z, Salati E, Timmins P, Lim S H. Tumor vaccine for ovarian carcinoma targeting sperm protein 17. Cancer 2002; 94(9):2447-2453.
53. Zhu J, Paul W E. Heterogeneity and plasticity of T helper cells. Cell Res; 20(1):4-12.
54. Murakami H, Ogawara H, Hiroshi H. Th1/Th2 cells in patients with multiple myeloma. Hematology 2004; 9(1): 41-45.
55. Garcia-Hernandez Mde L, Gray A, Hubby B, Klinger O J, Kast W M. Prostate stem cell antigen vaccination induces 56. Pantuck A J, van Ophoven A, Gitlitz B J, Tso C L, Acres B, Squiban P, Ross M E, Belldegrun A S, Figlin R A. Phase I trial of antigen-specific gene therapy using a recombinant vaccinia virus encoding MUC-1 and IL-2 in MUC-1-positive patients with advanced prostate cancer. J Immunother 2004; 27(3):240-253.
57. Allam M, Julien N, Zacharie B, Penney C, Gagnon L. Enhancement of Th1 type cytokine production and primary T cell activation by PBI-1393. Clin Immunol 2007; 125(3):318-327.
58. Lee S O, Pinder E, Chun J Y, Lou W, Sun M, Gao A C. Interleukin-4 stimulates androgenindependent growth in LNCaP human prostate cancer cells. Prostate 2008; 68(1): 85-91.
59. Ebelt K, Babaryka G, Figel A M, Pohla H, Buchner A, Stief C G, Eisenmenger W, Kirchner T, Schendel O J, Noessner E. Dominance of CD4+ lymphocytic infiltrates with disturbed effector cell characteristics in the tumor microenvironment of prostate carcinoma. Prostate 2008; 68(1): 1-10.
60. Ebelt K, Babaryka G, Frankenberger B, Stief C G, Eisenmenger W, Kirchner T, Schendel O J, Noessner E. Prostate cancer lesions are surrounded by FOXP3+, PD-1+ and B7-H1+ lymphocyte clusters. Eur J Cancer 2009; 45(9): 1664-1672.
61. Miller A M, Lundberg K, Ozenci V, Banham A H, Hellstrom M, Egevad L, Pisa P. CD4+ CD25high T cells are enriched in the tumor and peripheral blood of prostate cancer patients. J Immunol 2006; 177(10):7398-7405.

What is claimed is:

1. A composition comprising:
 a recombinant AKAP-4 tumor-associated antigen loaded antigen presenting cell that capable of generating an AKAP-4 specific cytotoxic T lymphocyte specific for one or more prostate cancer cells.

2. The composition of claim 1, wherein the antigen presenting cell is a dendritic cell.

3. The composition of claim 1, wherein the antigen presenting cell is an autologous dendritic cell.

4. The composition of claim 1, wherein the composition comprises a nucleotide sequence that codes for the recombinant AKAP-4 tumor-associated antigen.

5. An immunotherapy composition comprising an AKAP-4 tumor-associated antigen capable of generating an AKAP-4 specific cytotoxic T lymphocyte specific for one or more prostate cancer cell.

6. The immunotherapy composition of claim 5, further comprising at least one antigen presenting cell.

7. The immunotherapy composition of claim 6, wherein the antigen presenting cell is a dendritic cell.

8. The immunotherapy composition according to claim 5, wherein the at least one antigen presenting cell is a pulsed or loaded with the peptide or an expression construct encoding the AKAP-4 tumor-associated antigen.

* * * * *